(12) United States Patent
Lattner et al.

(10) Patent No.: US 7,879,920 B2
(45) Date of Patent: Feb. 1, 2011

(54) OXYGENATE TO OLEFIN MANUFACTURE AND RECOVERY PROCESS

(75) Inventors: James R. Lattner, Seabrook, TX (US); Christopher Becker, Russell, KS (US); Cor F. Van Egmond, Pasadena, TX (US); Andrew M. Argo, Albuquerque, NM (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1035 days.

(21) Appl. No.: 11/097,809

(22) Filed: Apr. 1, 2005

(65) Prior Publication Data
US 2006/0135632 A1  Jun. 22, 2006

Related U.S. Application Data

(60) Provisional application No. 60/639,170, filed on Dec. 22, 2004.

(51) Int. Cl.
*C07C 27/26* (2006.01)
(52) U.S. Cl. ............... 518/726; 585/638; 585/639; 585/640; 585/804; 585/809; 203/14; 203/18
(58) Field of Classification Search .......... 585/639, 585/640, 638, 804, 809; 518/726; 203/14, 203/18
See application file for complete search history.

(56) References Cited

U.S. PATENT DOCUMENTS

| | | | |
|---|---|---|---|
| 4,025,398 A * | 5/1977 | Haselden | 203/25 |
| 4,665,249 A | 5/1987 | Mao et al. | 585/408 |
| 4,777,321 A * | 10/1988 | Harandi et al. | 585/640 |
| 5,028,400 A | 7/1991 | Harandi et al. | 422/211 |
| 5,714,662 A | 2/1998 | Vora et al. | 585/640 |
| 6,403,854 B1 * | 6/2002 | Miller et al. | 585/638 |
| 6,495,609 B1 * | 12/2002 | Searle | 518/700 |
| 2003/0004386 A1 * | 1/2003 | Lattner et al. | 585/804 |
| 2003/0130555 A1 * | 7/2003 | Cheng et al. | 585/804 |
| 2004/0026801 A1 * | 2/2004 | Konijn et al. | 261/114.1 |
| 2004/0127758 A1 * | 7/2004 | Van Egmond | 585/324 |
| 2004/0127759 A1 | 7/2004 | Van Egmond | 585/327 |
| 2004/0127785 A1 * | 7/2004 | Davidson et al. | 600/407 |
| 2005/0107651 A1 * | 5/2005 | Sher et al. | 585/639 |

FOREIGN PATENT DOCUMENTS

| | | |
|---|---|---|
| EP | 0 289 234 | 2/1988 |
| WO | 2004/011404 | 5/2004 |

\* cited by examiner

*Primary Examiner*—Prem C Singh
(74) *Attorney, Agent, or Firm*—Kevin M. Faulkner; David M. Weisberg

(57) ABSTRACT

This invention is directed to methods for forming an olefin stream from a methanol stream. A lower grade methanol, such as chemical grade or crude methanol, can be used as feed to form the olefin stream. The process uses a relatively simple distillation type step to vaporize a portion of the methanol feed stream and send the resulting vapor stream to a reaction unit to form the olefin stream. In addition, the invention provides the ability to operate the downstream recovery units with reduced fouling or plugging due to the presence of fine solids components.

6 Claims, 2 Drawing Sheets

OXYGENATE TO OLEFIN MANUFACTURE AND RECOVERY PROCESS

CROSS REFERENCE TO RELATED APPLICATIONS

This application claims the benefit of Provisional Application No. 60/639,170 filed Dec. 22, 2004, the disclosure of which is fully incorporated herein by reference.

FIELD OF THE INVENTION

This invention is directed to using a low grade methanol stream as a feed stream for forming an olefin stream. The invention further includes a method for reducing solids fouling or plugging in the downstream product recovery vessels.

BACKGROUND OF THE INVENTION

Oxygenated hydrocarbons, particularly methanol, have been used as feedstock to produce light olefins such as ethylene and propylene. In one particular process, methanol is converted to an olefin product containing a significant amount of light olefins, such as ethylene and propylene, by contacting the methanol with a molecular sieve catalyst. This type of process has generally been referred to as a methanol to olefin (MTO) reaction process.

Methanol that is used as feed for the MTO reaction process is typically produced from natural gas. Initially, the natural gas is converted to a syngas, which is a gas containing hydrogen, carbon monoxide and carbon dioxide. The syngas is then converted catalytically to a methanol composition, producing substantial quantities of water as a by-product. The methanol composition is then de-watered to form a substantially pure methanol composition, which is then transported and used as feed for the MTO reaction process.

Efforts have been directed to integrating the manufacture of methanol feed streams with the conversion of the methanol to form light olefins. For example, U.S. Pat. No. 5,714,662 (Vora et al.), discloses integrating a methanol synthesis system with a MTO reaction system. The disclosed process passes a crude methanol stream directly to the MTO reaction system for the production of light olefins.

U.S. Patent Publication No. US 2004/0127759 A1 discloses a process for producing light olefins by integrating a methanol synthesis system with a MTO reaction system. The intetrated system implements a shared separation system for separating oxygenate components from the respective methanol synthesis system and the MTO reaction system.

New ways of integrating methanol synthesis and the conversion of the methanol to olefin are continuously sought. Such systems require rather large amounts of energy to operate and energy savings are of particular importance. In addition, methods of operating such integrated systems are particularly complex, and complex systems are prone to bottlenecks. Accordingly, new methods of reducing or eliminating bottlenecks in huge complex systems are also of considerable demand.

SUMMARY OF THE INVENTION

This invention provides methanol synthesis and methanol conversion processes that can be operated at considerable energy savings relative to conventional systems. The two systems can be combined with large energy savings and the methanol conversion process can be operated with reduced fouling or solids buildup that can occur as a result of catalyst carryover.

According to one aspect of the invention, there is provided a process for forming an olefin stream from a methanol stream. In one embodiment, the process includes a step of heating a liquid methanol composition to form a vapor stream that contains methanol and a liquid stream that contains water. The vapor stream is separated from the liquid stream, and at least a portion of the vapor stream is contacted with molecular sieve catalyst to form an olefin stream.

In another embodiment of the invention, the process for forming an olefin stream from a methanol stream includes heating a methanol composition to form a vapor stream and contacting at least a portion of the vapor stream with molecular sieve catalyst to form an olefin stream. At least a portion of the olefin stream is cooled to condense out a water stream, with the water stream generally containing a minor amount of oxygenated hydrocarbon and solid particles carried over from the methanol to olefin reaction process. The oxygenated hydrocarbon is preferably stripped from the water stream in a stripping column. In one embodiment, the stripping column has a plurality of trays and a liquid flow across each tray of at least 0.5 feet per second.

In one embodiment of the invention, the methanol composition that is manufactured and used to make olefin contains at least 0.1 wt. % water, based on total weight of the composition. Preferably, the methanol composition contains not greater than 12 wt % water, based on total weight of the composition.

In another embodiment, the olefin stream that is produced is cooled after it leaves the reactor to form an olefin vapor stream and a liquid water stream. Due to the olefin manufacture process, the liquid water stream will generally contain oxygenated hydrocarbon and solid particles. The solid particles will generally be molecular sieve catalyst particles. In particular, the solid particles will have a density greater than water. In more particular embodiments, the solid particles will have an average diameter of from 5 to 60 microns.

According to another aspect of the invention, there is provided a process that includes a step of heating a liquid methanol composition to form a vapor stream that contains methanol and a liquid stream that contains water. The vapor stream and liquid stream are separated from one another, and the separated liquid stream is stripped of oxygenated hydrocarbons in a stripping column. At least a portion of the separated vapor stream is further contacted with molecular sieve catalyst to form an olefin stream.

In one embodiment, the liquid stream formed from the methanol heating step and the liquid stream that contains the solids particles are sent to the same stripping column for stripping of hydrocarbon material in the predominantly water containing stream. Preferably, the stripping column has a plurality of trays and a liquid flow across each tray of at least 0.5 feet per second.

In another embodiment, at least a portion of the oxygenated hydrocarbons that are stripped in the stripping column are removed from the column and contacted with molecular sieve catalyst to form the olefin stream. This allows for recovery of oxygenated hydrocarbons that can be recycled and used in the feed stream. This also reduces the amount of hydrocarbons in water stream that leaves the stripping column, which allows the water stream to be sent directly to a waste water treatment system without a placing a high biological demand on the waste treatment system.

BRIEF DESCRIPTION OF THE DRAWING

Examples of various embodiments of this invention are shown in the attached Figures, wherein.

DETAILED DESCRIPTION OF THE INVENTION

I. Methanol Feed and Olefin Recovery

Figure 1:
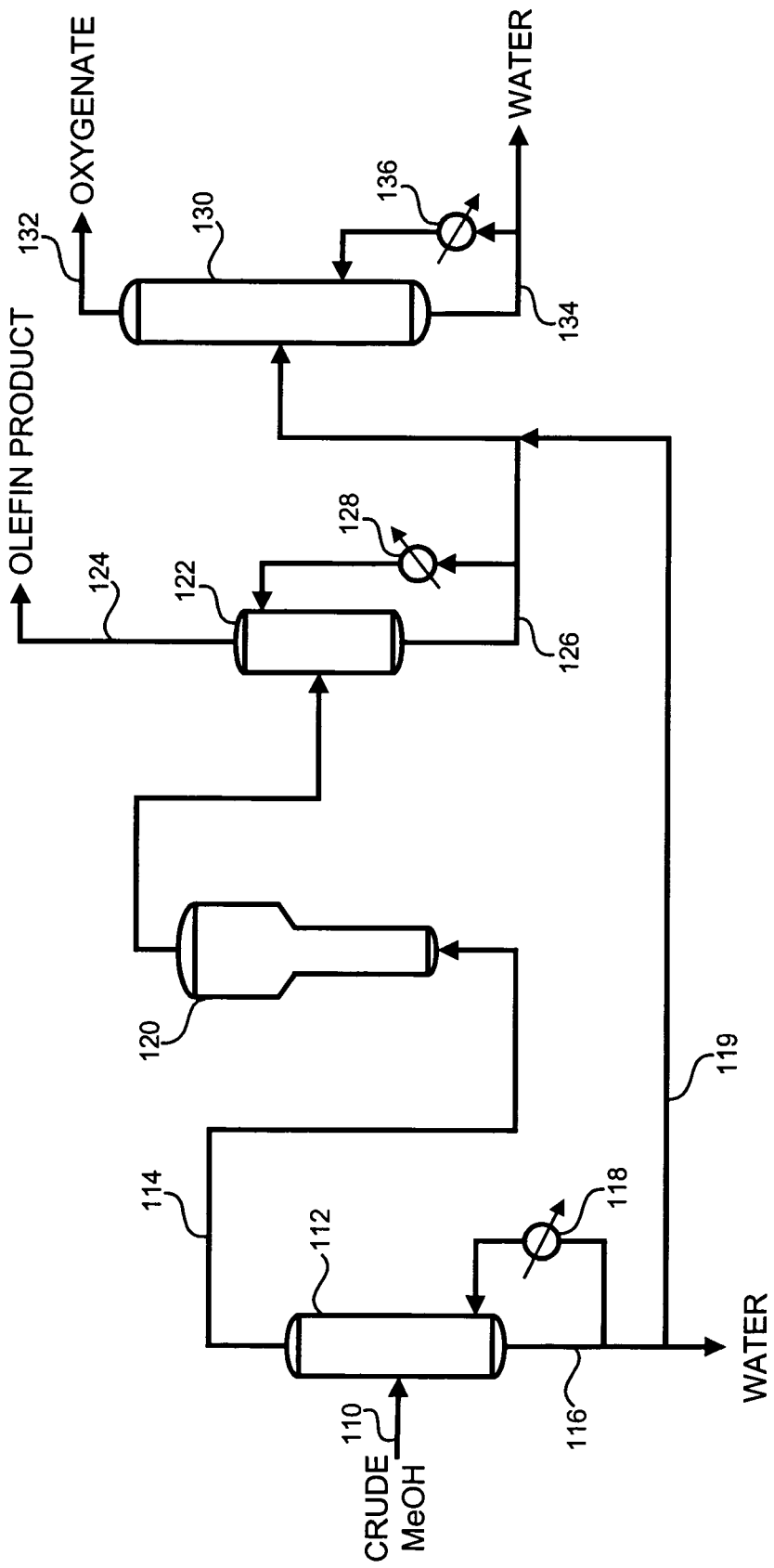
FIG. 1 is a flow diagram of one embodiment of the reaction and recovery system of the invention.

This invention is directed to methods for forming an olefin stream from a methanol stream. The invention provides an advantage in that generally lower grade methanol, such as chemical grade or crude methanol, can be used as feed to form the olefin stream. Although such streams contain significant amounts of water, it is not necessary to remove all of the water, since the water will not generally be detrimental to forming the desired olefin stream. In one embodiment of the invention, the process uses a relatively simple distillation type step to vaporize a portion of the methanol feed stream and send the resulting vapor stream to a reaction unit to form the olefin stream.

Another advantage provided by the invention is that the downstream recovery units can be operated with reduced fouling or plugging due to the presence of fine solids components. In general, the formation of olefin from methanol is accomplished by contacting the methanol with a molecular sieve catalyst in a reactor, preferably a fluidized bed type reactor. On occasion, this contact between sieve and catalyst results in a carry over of catalyst material with the olefin stream that leaves the reactor. Although the amount of catalyst material carried over is relatively small compared to the entire amount of catalyst used in the reaction system, it can accumulate in downstream vessels that handle various liquid streams, and plug the vessel. One aspect of the invention reduces and/or eliminates accumulation and plugging. In particular, one aspect of the invention incorporates the use of an oxygenate stripping column that can be operated with little to no plugging.

II. Making Methanol

A. Chemical Grade or Crude Type Methanol

The process of this invention uses a chemical grade or crude type of methanol feed. According to the invention, the methanol feed is a grade of methanol that is less pure than typical grade A or AA methanol. In particular, the methanol composition used as feed in this invention is a composition that contains less than 99.9% methanol by volume, based on total volume of the feed composition.

Methanol feed compositions useful in this invention can be manufactured from a variety of carbon sources. Examples of such sources include biomass, natural gas, $C_1$-$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention, natural gas is the preferred hydrocarbon feed source.

One way of converting the carbon source to a methanol composition is to first convert the carbon source to synthesis gas (syngas), and then converting the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

Synthesis gas comprises carbon monoxide and hydrogen. Optionally, carbon dioxide and nitrogen are included. Conventional processes for converting carbon components to syngas include steam reforming, partial oxidation, and autothermal reforming.

The hydrocarbon feed stream that is used in the conversion of hydrocarbon to synthesis gas, is optionally treated to remove impurities that can cause problems in further processing of the hydrocarbon feed stream. These impurities can poison many conventional propylene and ethylene forming catalysts. A majority of the impurities, which may be present, can be removed in any conventional manner. The hydrocarbon feed is preferably purified to remove sulfur compounds, nitrogen compounds, particulate matter, other condensables, and/or other potential catalyst poisons prior to being converted into synthesis gas.

In one embodiment of the invention, the hydrocarbon feed stream is passed to a synthesis gas plant. Synthesis gas refers to a combination of hydrogen and carbon oxide produced in a synthesis gas plant from a hydrocarbon feed, the synthesis gas having an appropriate molar ratio of hydrogen to carbon oxide (carbon monoxide and/or carbon dioxide), as described below. The synthesis gas plant may employ any conventional means of producing synthesis gas, including partial oxidation, steam or $CO_2$ reforming, or some combination of these two chemistries.

Steam reforming generally comprises contacting a hydrocarbon with steam to form synthesis gas. The process preferably includes the use of a catalyst.

Partial oxidation generally comprises contacting a hydrocarbon with oxygen or an oxygen containing gas such as air to form synthesis gas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional synthesis gas-generating processes include gas phase partial oxidation, autothermal reforming, fluid bed synthesis gas generation, catalytic partial oxidation and various processes for steam reforming.

B. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \rightleftharpoons CO + 3H \tag{1}$$

or

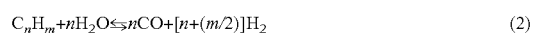
$$C_nH_m + nH_2O \rightleftharpoons nCO + [n+(m/2)]H_2 \tag{2}$$

and

$$CO + H_2O \rightleftharpoons CO_2 + H_2 \tag{3 shift reaction}$$

The reaction is carried out in the presence of a catalyst. Any conventional reforming type catalyst can be used. The catalyst used in the step of catalytic steam reforming comprises at least one active metal or metal oxide of Group 6 or Group 8-10 of the Periodic Table of the Elements. The Periodic Table of the Elements referred to herein is that from *CRC Handbook of Chemistry and Physics*, $82^{nd}$ Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. Preferably, the catalyst includes from about 5 wt % to about 25 wt % of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Syngas

The invention further provides for the production of synthesis gas, or CO and $H_2$, by oxidative conversion (also referred to herein as partial oxidation) of hydrocarbon, particularly natural gas and $C_1$-$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightarrows nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminium titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ $cm^3/g \cdot hr$ to about $10^5$ $cm^3/g \cdot hr$ for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO + H_2O \leftrightarrows H_2 + CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

E. Converting Syngas to Methanol

The synthesis gas is sent to a methanol synthesis process and converted to a methanol composition. The methanol synthesis gas process is accomplished in the presence of a methanol synthesis catalyst.

In one embodiment, the synthesis gas is sent as is to the methanol synthesis process. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides ($CO+CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas.

Desirably, the stoichiometric molar ratio is sufficiently high so as maintain a high yield of methanol, but not so high as to reduce the volume productivity of methanol. Preferably, the synthesis gas fed to the methanol synthesis has a stoichiometric molar ratio (i.e., a molar ratio of $H_2:(2CO+3CO_2)$) of from about 1.0:1 to about 2.7:1, more preferably from about 1.1 to about 2.0, more preferably a stoichiometric molar ratio of from about 1.2:1 to about 1.8:1.

The $CO_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the synthesis gas formed in the synthesis gas conversion plant is cooled prior to sending to the methanol synthesis reactor. Preferably, the synthesis gas is cooled so as to condense at least a portion of the water vapor formed during the synthesis gas process.

The methanol synthesis process used to manufacture the methanol composition of this invention can be any conventional process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$$CO+2H_2 \rightarrow CH_3OH$$

$$CO_2+3H_2 \rightarrow CH_3OH+H_2O$$

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

F. Methanol for Use as Feed

Preferably, the methanol composition that is recovered from the methanol manufacturing process is sent directly to a methanol to olefins reaction system, and the methanol and other oxygenated hydrocarbons in the methanol feed are converted to olefin. In general, the methanol feed composition that is used in this invention contains less than 99.85 wt % methanol, based on total weight of the composition. Optionally, the methanol feed is supplemented with other oxygenates, such as alcohols, particularly ethanol, and/or aldehydes, which are particularly suited for use as a feed component in the catalytic conversion of the oxygenates to olefins.

In one embodiment of the invention, the methanol feed composition comprises at least about 50 wt % methanol, based on total weight of the composition. Desirably, the methanol feed composition comprises at least about 75 wt % methanol, preferably at least about 80 wt % methanol, more preferably at least about 85 wt % methanol, and most preferably at least about 90 wt % methanol, based on total weight of the composition.

In another embodiment of the invention, the methanol feed composition comprises not greater than 99 wt % methanol, based on total weight of the composition. Preferably, the methanol feed composition comprises not greater than 98 wt % methanol, more preferably not greater than 97 wt % methanol, and most preferably not greater than 96 wt % methanol, based on total weight of the composition.

Typically, the methanol feed composition includes at least some water. The water content should not be so high that shipping costs are prohibitive, but of sufficient quantity to exert a positive partial pressure in the methanol to olefin conversion reaction, thereby increasing selectivity to ethylene and/or propylene. Desirably, the water content is at least about 0.1 wt %, based on total weight of the methanol composition. Preferably, the methanol composition contains at least about 0.5 wt % water, more preferably at least about 1.0 wt % water, and most preferably at least about 1.5 wt % water, based on total weight of the methanol composition.

In another embodiment, the methanol feed composition contains not greater than about 12 wt % water, based on total weight of the methanol composition. Preferably, the methanol composition contains not greater than about 10 wt % water, more preferably not greater than about 8 wt % water, and most preferably not greater than about 5 wt % water, based on total weight of the methanol composition.

III. Process for Making Olefin

A. General Process Description

The methanol feed stream is preferably fed directly to an olefin conversion process or it can be transported in large quantities over great distances converted to olefins. According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment of the invention, the methanol composition is converted to olefins by contacting the methanol composition with an olefin forming catalyst to form the olefin product. The olefin product is recovered, and water, which forms during the conversion of the oxygenates in the methanol to olefins, is removed. After removing the water, the olefins are separated into individual olefin streams, and each individual olefin stream is available for further processing.

B. Description of Olefin Forming Catalyst

Any catalyst capable of converting oxygenate to olefin can be used in this invention. Molecular sieve catalysts are preferred. Examples of such catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (Li- APSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [$MeO_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. Pat. No. 6,812,372 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., *Stud. Surf. Sci. and Catal.*, 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, η-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix materials. Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays.

Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

C. General Conditions for Converting Methanol to Olefins

According to the reaction process of this invention, the methanol composition is contacted with olefin forming catalyst to form an olefin stream, preferably containing a substantial amount of light olefins such as ethylene and/or propylene. The process for converting the oxygenate feedstock is, preferably, a continuous fluidized bed process, and most preferably a continuous high velocity fluidized bed process.

The reaction process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

One preferred reactor type is a riser reactor. These types of reactors are generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment of the invention, a fluidized bed process or high velocity fluidized bed process includes a reactor system, catalyst separation system, and a regeneration system. The reactor system preferably is a fluid bed reactor system. In one embodiment, the fluid bed reactor system has a first reaction zone within one or more riser reactors, and a second reaction zone within at least one catalyst separation vessel, preferably comprising one or more cyclones. In one embodiment, one or more riser reactors and catalyst separation vessel is contained within a single reactor vessel.

The average reaction temperature employed in the conversion process, specifically within the reactor, is of from about 250° C. to about 800° C. Preferably the average reaction temperature within the reactor is from about 250° C. to about 750° C.; more preferably, from about 300° C. to about 650° C.; yet more preferably from about 350° C. to about 600° C.; and most preferably from about 400° C. to about 500° C.

The pressure employed in the conversion process, specifically within the reactor, is not critical. The reaction pressure is based on the partial pressure of the feedstock exclusive of any diluent therein. Typically the reaction pressure employed in the process is in the range of from about 0.1 kpaa to about 5 MPaa, preferably from about 5 kPaa to about 1 MPaa, and most preferably from about 20 kpaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor is preferably sufficient to fluidize the molecular sieve catalyst composition within a reaction zone of the reactor. The SGV in the process, particularly within the reactor system, more particularly within a riser reactor, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

According to one embodiment, the conversion of methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

It is desirable to maintain an amount of coke on the catalyst in the reaction vessel to enhance the formation of desired olefin product, particularly ethylene and propylene. It is particularly desirable that the catalyst in the reactor be maintained to contain at least about 1.5 wt % coke. Preferably, the amount of coke maintained on the catalyst in the reactor should be from about 2 wt % to about 30 wt %.

III. Olefin Recovery

A. General Recovery

The methanol and other oxygenated hydrocarbons entering the reactor system are preferably converted, partially or fully, in a reactor zone forming an olefin vapor stream and a coked catalyst. In a fluidized reactor system, the olefin vapor stream and coked catalyst are sent to a catalyst separation vessel where the coked catalyst is separated from the vapor portion of the stream.

In a preferred embodiment, cyclones within the separation vessel are used to separate the coked catalyst composition. Gravity effects within the disengaging vessel can also be effective in separating the catalyst. Other processes for separating the catalyst from the gaseous effluent include the use of plates, caps, elbows, and the like.

In one embodiment, olefin and other product gases are separated from the catalyst and withdrawn from the reactor, then passed through a recovery system. Any conventional recovery system, technique and/or sequence useful in separating olefin(s) and purifying olefin(s) from other gaseous components can be used in this invention. Examples of recovery systems include one or more or a combination of various separation, fractionation and/or distillation towers, columns, and splitters, and other associated equipment; for example, various condensers, heat exchangers, refrigeration systems or chill trains, compressors, knock-out drums or pots, pumps, and the like.

Non-limiting examples of distillation towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene ($C_2$) splitter, propylene ($C_3$) splitter, butene ($C_4$) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

The oxygenate to olefin process forms a substantial amount of water as a by-product. Much of this water by-product can be removed prior to distillation by cooling the stream to a temperature below the condensation temperature of the water vapor in the stream. Preferably, the temperature of the product stream is cooled to a temperature below the condensation temperature of the oxygenate feed. In certain embodiments it is desirable to cool the product stream below the condensation temperature of methanol.

It is desirable to cool the olefin stream from the oxygenate to olefin reaction process, then separate the cooled olefin stream into a condensed, water containing stream and an olefin vapor stream. The condensed, water containing stream comprises most of the water from the olefin stream, and a significant portion of the oxygenated hydrocarbons from the olefin stream. The olefin vapor stream comprises a majority of the olefins, e.g., ethylene and propylene.

In one aspect of the invention, the olefin stream from the oxygenate to olefin reaction process is cooled so that a vapor stream, rich in olefins, can be separated from the condensed water containing stream. It is desirable that the vapor stream contain not greater than about 20 wt % water, preferably not greater than about 15 wt % water, more preferably not greater than about 12 wt % water. The vapor stream is then distilled so as to separate out propane and dimethyl ether.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column. Following quench, the effluent is compressed using equipment and techniques known to a person of ordinary skill in the art.

Example of Methanol Preheat and Olefin Recovery

An example of the overall aspect of the invention is shown in FIG. 1. According to FIG. 1, crude methanol is sent through a line 110 to a separator or distillation column 112. The crude methanol is in liquid form and is heated in the distillation column 112 by way of a heat exchanger 118 to form a vapor stream rich in methanol that exits the top of the column 112 through a line 114. The remaining liquid, which contains a significant amount of water, exits the column 112 through a line 116. A portion of the water stream flowing through the line 116 is recycled back to the distillation column 112 and heated by the heat exchanger 118.

The methanol vapor stream in the line 114 is sent to a methanol to olefins reaction unit 120, where the vapor stream contacts molecular sieve catalyst to form an olefin stream. Within the olefin reaction unit 120, the catalyst is separated from the olefin stream. The olefin stream is recovered as a vapor and sent to a quench vessel 122, where at least a portion of the water in the vapor stream is condensed. The remaining vapor stream is rich in olefin and is removed as an olefin product stream through a line 124 for further processing.

The condensed water stream in the quench vessel 122 is removed by way of a line 126. This condensed water stream contains some hydrocarbon entrained in the water during condensation and solid catalyst particles that were carried over with the olefin vapor stream from the olefin reaction unit 120.

A portion of the condensed water stream in line 126 is recycled back to the quench column 122 by way of a cooler 128. The remainder of the condensed water stream is sent to an oxygenate stripper 130. Oxygenate is removed as a vapor by way of a line 132, and the remaining liquid water stream is removed from the oxygenate stripper 130 through a line 134. A portion of the water in the line 134 is recycled back to the stripper 130 through a heat exchanger 136. Although not shown in FIG. 1, at least a portion of the oxygenated hydrocarbons stripped in the stripping column 130 can be recycled as feed. For example, the stripped oxygenate can be sent to the distillation column 112 and heated with the crude liquid methanol composition to form the vapor stream and liquid stream. As another example, at least a portion of the oxygenated hydrocarbon stripped in the stripping column 130 can be sent directly to the olefin reaction unit 120 and contacted with molecular sieve catalyst to form the olefin stream.

The stripper 130 can also be used to remove contaminants from other water streams. As on example in FIG. 1, at least a portion of the water stream from the distillation column 112 that passes through the line 116 can be sent through a line 119 and into stripper 130. This additional treatment of the water stream from the distillation column 112 is beneficial in that the oxygenated hydrocarbon content in the water stream can be further lowered, thereby lowering the biological demand on any subsequent waste water treatment system.

B. Solids Removal

In fluidized bed reaction systems, it is often difficult to completely separate all of the vapor product from the solid catalyst in the catalyst separation vessel. Certain of the catalyst particles are relatively small and are difficult to completely remove using typical separation techniques. Thus, it is quite common for catalyst particles to carry over with the separated vapor product from the catalyst separation vessel. As this vapor is then cooled to condense and separate out water from the olefin portion of the stream, the solid catalyst particles tend to separate out with the condensed water. If the solids content is significant, then problems can occur in further downstream processing, particularly in stripping units, where it is desirable to strip out hydrocarbon also entrained in the condensed water stream. At least one aspect of this invention, is directed to reducing or preventing problems associated with solids accumulating in this type of stripping unit.

In one aspect of the invention, vapor from the reactor portion of the reactor system is cooled to condense at least a portion of the water in the vapor, with the condensed water stream containing hydrocarbon and solid catalyst particles. This condensed water stream is then sent to a stripping column and at least a portion of the hydrocarbon is stripped out of the condensed stream. The stripped hydrocarbon can be re-used as feed if desired, and the stripped water stream is preferably sent to a waste treatment system.

In one embodiment, the condensed water stream contains oxygenated hydrocarbon. Examples of oxygenated hydrocarbon include one or more of the oxygenated hydrocarbons found in the methanol feedstream. Such hydrocarbons include alcohols and ethers, particularly methanol and/or dimethyl ether. The condensed water stream can include at least 50 wppm oxygenated hydrocarbon, based on total weight of the condensed water stream. In general the condensed water stream includes from about 100 wppm to 20,000 wppm oxygenated hydrocarbon, and more particularly from about 200 wppm to 10,000 wppm oxygenated hydrocarbon.

The solid particles in the condensed water stream are typically catalyst type fines that were not removed upstream of where condensation is carried out. Such solid particles have a density greater than that of water. Typically, the solid particles have a density of at least 1.1 gm/cc, more generally at least 1.2 gm/cc, and particularly at least 1.3 gm/cc. Such particles can be fairly dense, but the density is generally not greater than 2.5 gm/cc.

The catalyst particles in the condensed water stream typically have an average diameter that is less than that of the catalyst particles found in the reactor vessel. In general, the average diameter of the solid catalyst particles in the condensed water stream is less than half the average diameter of the solid catalyst particles in the reactor vessel. Typically, the average diameter of the solid particles in the condensed water stream is from about 5 to 60 microns, more generally from about 10 to 50 microns, and more likely from about 15 to 30 microns.

According to one aspect of the invention, the stripping unit includes at least one distillation column. Preferably, the distillation column has a plurality of trays that are designed to minimize plugging. In particular, each tray should have a deck area that has continuous liquid flow. Preferably, liquid flow across each tray is at least 0.5 feet per second, more preferably at least 0.6 feet per second, and most preferably at least 0.7 feet per second. Any type of tray can be used, such as bubble cap trays, valve trays and sieve trays. However, sieve trays are preferred.

Example of Solids Removal

Figure 2:
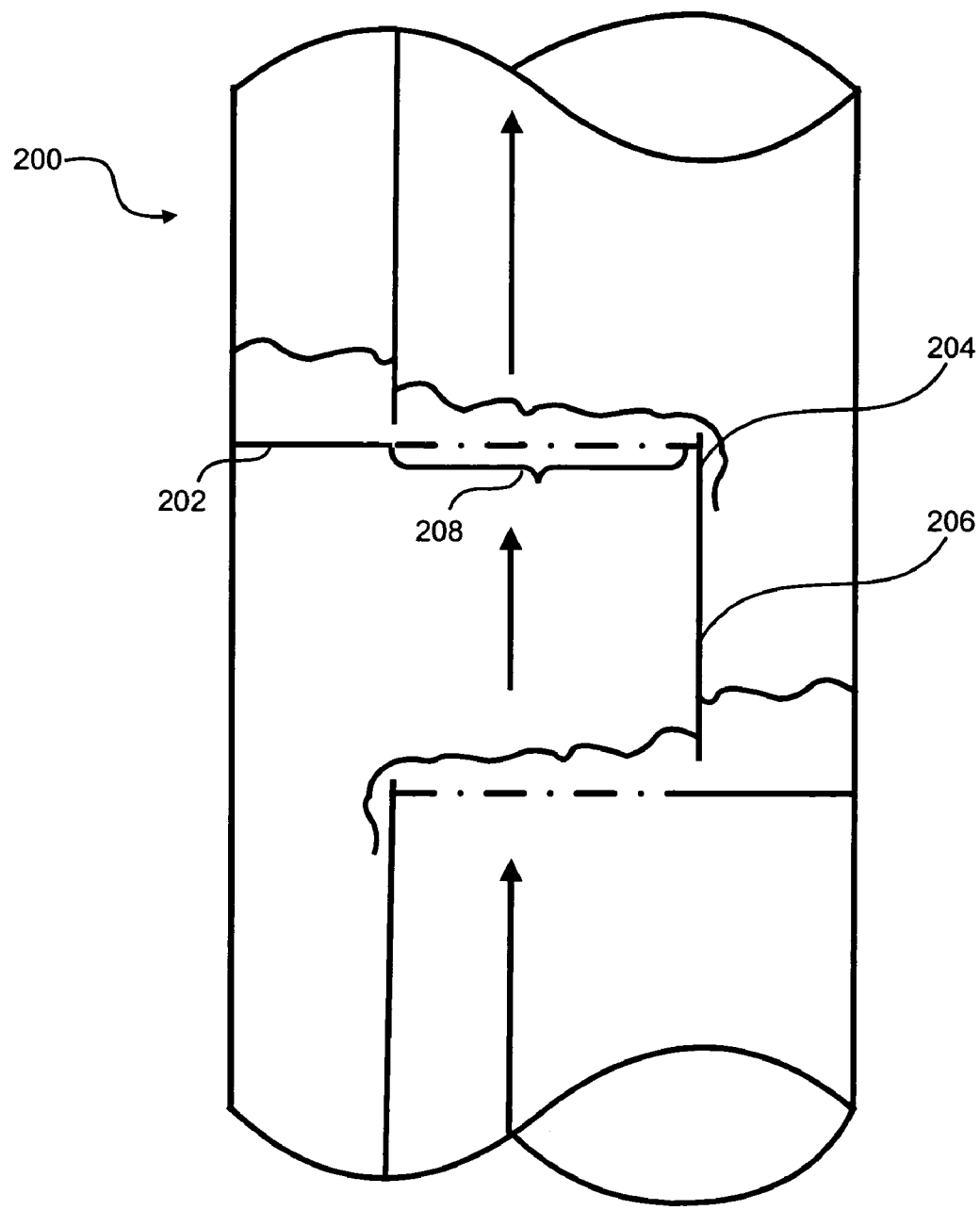
FIG. 2 is a simple sectional diagram of an oxygenate stripping column that can be used with the invention.

A preferred embodiment of the oxygenate stripper is shown in FIG. 2. According to the embodiment shown, distillation or stripping column 200 includes a plurality of trays, exemplified by tray 202. Tray 202 includes a weir 204 and a downcomer 206. The condensed water stream containing the solid particles passes across the weir 204 and down the downcomer 206 by gravity from one tray to the one below it. It is preferred that weir 204 be of such height that allows for some liquid (holdup) on the tray, but that the weir not be so high to reduce the desired liquid flow. Otherwise, the solids in the liquid will tend to settle out, and the column can plug.

Vapor, formed by evaporation of a portion of the liquid, preferably the oxygenated hydrocarbon portion of the water stream, flows up the column 200 and passes through the liquid via openings or holes on each tray. This area allows for the passage of vapor on each tray and is called the active tray area 208. As long as the holes across the active area 208 are suitably designed for the desired amount of vapor passage, any solids material in the liquid will be transported with the liquid across the weirs and down the downcomers, eventually exiting as a bottoms stream from the stripping column, and plugging of the column will be minimized.

C. Use of Olefin Streams

The ethylene and propylene streams produced and recovered according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_2$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

Having now fully described this invention, it will be appreciated by those skilled in the art that the invention can be performed within a wide range of parameters within what is claimed, without departing from the spirit and scope of the invention.

We claim:

1. A process for forming an olefin stream from a methanol stream, comprising:
   a) providing a methanol composition heated by a methanol synthesis reaction to form a vapor stream that contains methanol and a liquid stream that contains water, wherein the methanol composition contains at least 0.1 wt % water and not greater than 12 wt % water, based on total weight of the methanol composition;
   b) separating the vapor stream from the liquid stream, and sending at least a portion of the vapor stream directly to contact a molecular sieve;
   c) contacting at least a portion of the vapor stream with molecular sieve catalyst to form an olefin stream;
   d) cooling the olefin stream to form an olefin vapor stream and a liquid water stream, with the liquid water stream containing oxygenated hydrocarbon and solid particles; and
   e) wherein the liquid stream separated in step b) is stripped of oxygenated hydrocarbons in one stripping column, wherein the stripping column has a plurality of trays including a weir and a downcomer;
   wherein the condensed water stream containing the solid particles passes across the weir and down the downcomer by gravity from one tray to the one below it, the weir being of a height no more than 5% above the tray relative to the total length of the weir and downcomer to allow for a liquid holdup on the tray to maintain a liquid flow across each tray of at least 0.5 feet per second, where the downcomer is a length that is at least 90% the distance between adjoining trays; and
   wherein oxygenated hydrocarbon vapor, formed by evaporation of a portion of the liquid, flows up the column and passes through the liquid via openings or holes on each tray, and wherein valve or bubble trays and the like are absent and the openings or holes are present in only the first ⅔ of the length of the tray from the center.

2. The process of claim 1, wherein the solid particles are molecular sieve catalyst particles.

3. The process of claim 1, wherein the solid particles have a density greater than water.

4. The process of claim 1, wherein the solid particles have an average diameter of from 5 to 60 microns.

5. The process of claim 1, wherein at least a portion of the oxygenated hydrocarbons stripped in the stripping column is heated with the liquid methanol composition to form the vapor stream and liquid stream.

6. The process of claim 1, wherein at least a portion of the oxygenated hydrocarbons stripped in the stripping column is contacted with molecular sieve catalyst to form the olefin stream.

* * * * *